United States Patent [19]

Shuffield

[11] Patent Number: 4,516,578
[45] Date of Patent: May 14, 1985

[54] RECTAL DEVICE AND METHOD OF INSERTING SAME

[76] Inventor: Luther Shuffield, 4005 Twilight Dr., Fort Worth, Tex. 76116

[21] Appl. No.: 526,410

[22] Filed: Aug. 25, 1983

Related U.S. Application Data

[63] Continuation-in-part of Ser. No. 429,815, Sep. 30, 1982, Pat. No. 4,471,782.

[51] Int. Cl.³ .............................................. A61M 26/00
[52] U.S. Cl. .................................. 128/341; 128/1 R; 128/343; 604/104
[58] Field of Search ...................... 128/1 R, 4, 303.11, 128/DIG. 25, 26, 79, 341-343, 127; 604/15-18, 29, 96, 104-106, 278, 327-330, 338-339, 347-348, 15

[56] References Cited

U.S. PATENT DOCUMENTS

| | | | |
|---|---|---|---|
| 2,711,173 | 6/1955 | Seidler | 604/15 |
| 3,331,371 | 7/1967 | Rocchi et al. | 604/246 |
| 3,469,575 | 9/1969 | Vass et al. | 604/278 |
| 3,866,601 | 2/1975 | Russell | 604/271 |
| 3,870,048 | 3/1975 | Yoon | 128/303.1 |
| 4,198,978 | 4/1980 | Nigro | 604/15 |
| 4,286,593 | 9/1981 | Place et al. | 128/127 |
| 4,318,404 | 3/1982 | Cunningham | 604/15 |

*Primary Examiner*—Lee S. Cohen
*Assistant Examiner*—Steven Falk
*Attorney, Agent, or Firm*—Larson and Taylor

[57] ABSTRACT

A rectal device and a method of inserting same. The tube has a resilient diaphragm connected thereto and extending transversely therefrom to block escape of the liquid being introduced. The diaphragm comprises a stiff outer ring and a more pliable central portion, the latter preferably including stiffening means in the form of ribs, fins or the like. For insertion, the diaphragm is wrapped around the tube and placed in an inserter tube having a rounded expandable distal end. After the whole assembly is inserted, the inserter tube is removed by sliding it down over the rectal device. The rectal device may comprise relatively movable inside an outer tubes with struts connecting the diaphragm to the distal end of the inside tube. After procedure is completed, whether using barium or cleansing enema, the diaphragm is then removed by slowly but firmly pulling on the removal cord. The diaphragm folds itself around the infusion tube for easy removal.

26 Claims, 15 Drawing Figures

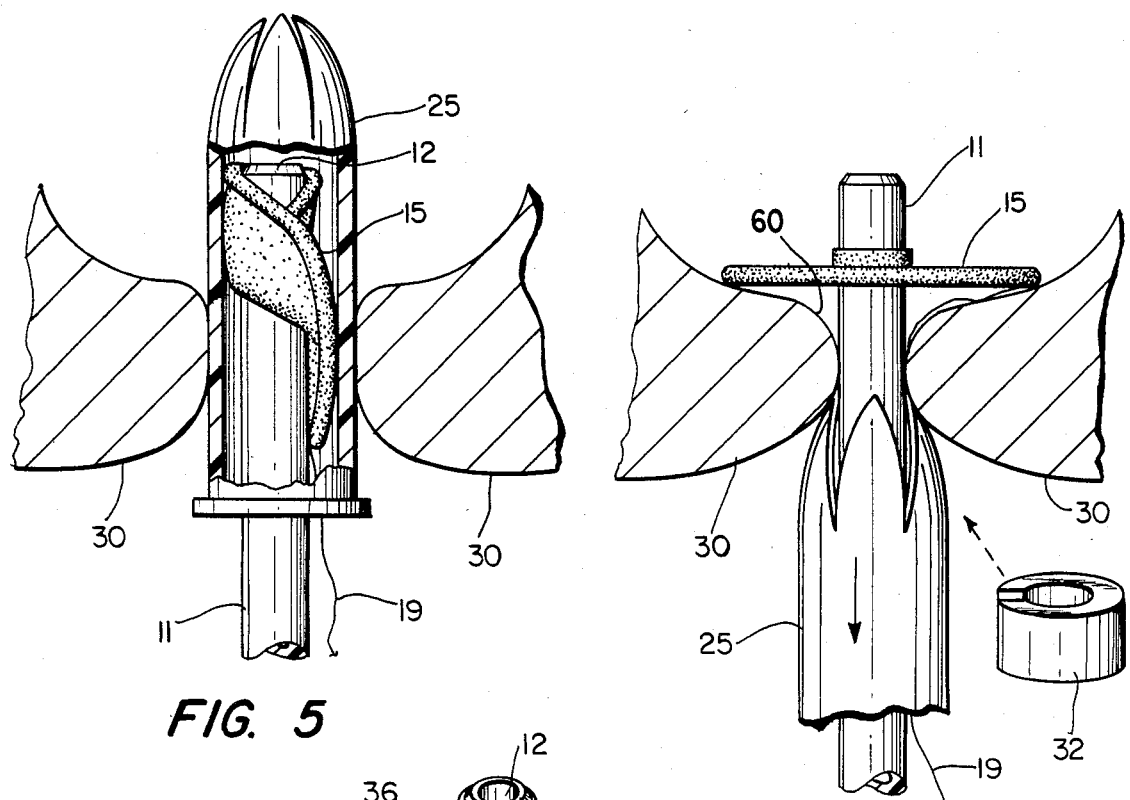
FIG. 5
FIG. 6
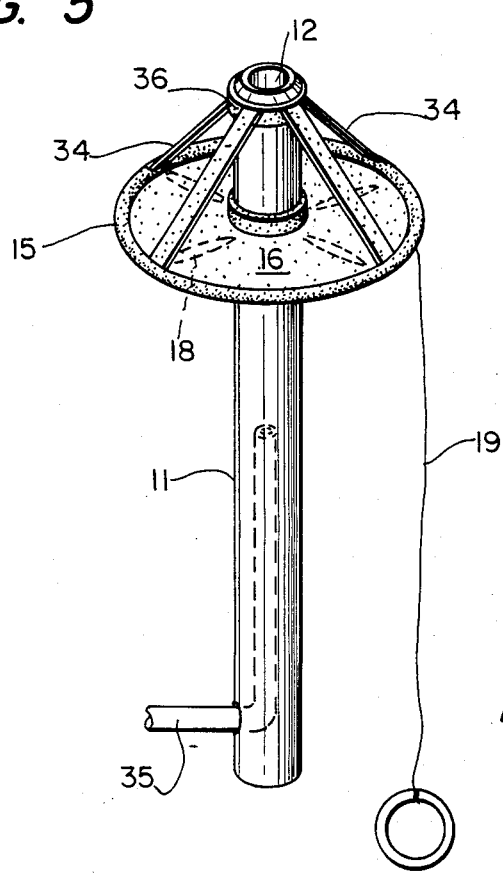
FIG. 7

RECTAL DEVICE AND METHOD OF INSERTING SAME

RELATED APPLICATION

This application is a continuation-in-part of my previous application Ser. No. 429,815, filed Sept. 30, 1982, now U.S. Pat. No. 4,471,782.

BACKGROUND OF THE INVENTION

This invention relates to a rectal device intended primarily for introducing into the anal opening suitable fluids such as enema liquids, barium or air, the latter two fluids for X-ray examination purposes.

In use, it is necessary to provide a means for positively retaining the distal end of these devices in the rectum and to prevent the escape of the fluid being introduced. The most common technique is to utilize an inflatable balloon in the vicinity of that distal end. With the balloon deflated, the device is introduced into the anal opening. Then, after the balloon and the distal end are located inside the rectum the balloon is inflated so as to prevent removal thereof and to prevent the escape of the liquid, while carrying out the relevant medical procedure.

However, balloons of this type have a distinct disadvantage. Obviously, the balloon is not visible to the medical operator. Hence, inflating of the balloon will often involve an element of guess work. An over inflated balloon can cause severe damage including rupturing of the rectum wall which, because of infection, can result in death. If the balloon is under inflated, then it will not carry out its function of holding the device within the rectum and concurrently preventing leakage of liquid around the outside of the balloon and through the anal opening.

Certain other devices are also known wherein means other than inflatable balloons are utilized for holding the device within the rectum. These include for example the Ronnquist U.S. Pat. No. 4,030,500 and the Vass U.S. Pat. No. 3,469,575. These references show stiff annular rings, i.e. they are not imperforate disks of the type utilized to both position the rectal infusion device within the rectum and also prevent the escape of the fluid being introduced.

Hence, there exists a need for a rectal device of the type having a portion retained in the rectum to both position the device and prevent the escape of the introduced fluid, which can be easily introduced and yet safely, comfortably and efficiently carry out the intended function of positioning the device within the rectum and preventing the escape of the fluid being introduced therethrough.

SUMMARY OF THE INVENTION

Hence, it is a purpose of the present invention to provide a new and improved rectal device of the type having means for introducing a fluid into the rectum, for positioning itself within the rectum to prevent removal thereof and/or for preventing the escape of the liquid being introduced, or other substances located within the rectum. The present invention also includes a new and improved technique for conveniently and comfortably introducing the device through the anal opening into the person's rectum.

These purposes of the present invention are achieved by providing a rectal device comprising an elongated tube and an imperforate diaphragm attached thereto near the distal end thereof, which diaphragm includes a stiff outer ring and a more pliable central portion between the ring and the tube. Suitable means are normally provided to assist in stiffening the central portion. The diaphragm is sufficiently stiff such that it normally assumes a position generally flat and transverse to the axis of the tube, and yet sufficiently resilient that it can be folded up or wrapped around the tube to facilitate insertion of the device into the anal opening.

In one embodiment, the device comprises a single tube while in another embodiment the device may comprise a pair of concentric tubes, the inside tube being axially slideable relative to the outside tube such that two fluids can be introduced therethrough, one through the inside tube and the other between the inside and outer tubes. In the two tube embodiment, the diaphragm would be attached to the outer tube.

In either embodiment of the invention, the central portion may include additional stiffening means which may take different forms. In one form, the additional stiffening means may comprise either ribs or upstanding fins formed integrally with the diaphrgam, i.e. formed during the process of moulding the diaphragm, the ribs or fins preferably extending in radial directions. Another form of the stiffening means may comprise band struts extending from the outer periphery of the diaphragm to the distal end of the tube. In the two tube embodiment, these bands would extend from the outer periphery of the diaphragm to the distal end of the inside tube.

The two-tube embodiment with strut stiffening means has the advantage of allowing the diaphragm to collapse which would lend itself to easier insertion After the diaphragm is positioned above the internal sphincter muscles, the inner tube can be pushed forward causing the diaphragm to become transverse to the infusion tube which would enable proper seating of the diaphragm.

The diaphragm may take many different forms, so long as it maintains its characteristics of being sufficiently stiff to normally assume its transverse position within the rectum and yet sufficiently resilient to be folded up and wrapped around the tube for insertion. Generally this requires that the outer periphery of the diaphragm be formed as a relatively stiff ring. This stiffness can be provided by constructing the outer periphery of the diaphragm as an enlarged, more stiff portion or alternatively the outer periphery can be filled with a fluid.

Another feature of the present invention is the new and improved means and method for inserting the device into the rectum. As described above, the diaphragm is capable of being folded up and wrapped around the tube. In this form the device is inserted within an inserter tube which has a rounded but expandable distal end. In addition especially with the fin type stiffening means, but also to some extent with the other embodiments the diaphragm can be pushed straight forward into the inserter with a twisting motion which will fold the fins around the infusion tube. The inserter tube, with the device therein, is then inserted through the anal opening, carrying the device past the anal sphincter muscles. Thereafter, the inserter tube is removed by sliding it down over the device, whereby the said expandable end of the inserter tube expands to pass over the device. The diaphragm and distal end of the device are then in place within the rectum, the inserter tube is slid completely off of the device and discarded, and the proximal end of the infusion tube is then connected to a line for receiving the liquid to be introduced.

Although the invention is intended primarily for the introduction of fluids into the rectum, it has other uses. One such use is as an occluder. After the diaphragm is inserted into the rectum and seated on the rectal sling above the internal sphincter muscle, the tube can then be clamped. The diaphragm would then act as an occluder, simply preventing escape of any substances such as fecal materials, whether solid, liquid or gaseous, through the anal opening. This would serve people who suffer from fecal incontinence. The occlusive diaphragm would allow fecally incontinent people to function in public without the embarrasement of untimely bowel movements. With this concept, the fecally incontinent person would be able to schedule bowel movements at his or her own convenience. The present invention, as an occouder, could also be used to retain certain medications within the rectum, which medications would otherwise be expelled.

. Another use of the present invention is for purposes of colonic feeding.

Hence, it is an object of the present invention to provide a new and improved rectal device.

It is another object of the present invention to provide a new and improved rectal device having means for retaining the device in the rectum and preventing the escape of the fluid being introduced, and which has improved comfort, safety and efficiency.

It is another object of the present invention to provide a new and improved rectal infusion device having an imperforate diaphragm near the distal end thereof, which diaphragm is sufficiently stiff that the diaphragm will normally assume a position transverse to the tube and yet sufficiently resilient that is can be folded up and wrapped around the tube to facilitate insertion.

It is another object of the present invention to provide a new and improved means and method for introducing a rectal infusion device of the type described, wherein the device is placed within an inserter tube having an expandable distal end which, after introduction, can be slid down over the device to be discarded.

It is another object of the present invention to provide a rectal infusion device having a diaphragm of the type described, which diaphragm has additional means to assist stiffening thereof.

It is another object of the present invention to provide a new and improved rectal infusion device of the type described which has a pair of concentric tubes, the inside tube being slideable relative to the outer tube, to facilitate introduction of two different fluids, wherein the diaphragm is attached to the outer tube and means are provided for limiting movement of the inside tube axially relative to the outside tube.

It is still another object of the present invention to provide a new and imporved rectal occulsive device capable of holding substances within the rectum to prevent unintended escape thereof.

These and other objects of the present invention will become apparent from the detailed description to follow, taken together with the accompanying drawings.

BRIEF DESCRIPTION OF THE DRAWINGS

There follows a detailed description of the perfered embodiments of the invention, which description is to be read together with the accompanying drawings, wherein:

FIGS. 5 and 6 are side elevational views, with FIG. 5 partially cut away, illustrating a method of introducing the rectal device of the present invention through the anal opening and into the rectum.

FIG. 7 is a perspective view similar to FIG. 1 but showing a modification of the present invention.

DETAILED DESCRIPTION OF THE PREFERRED EMBODIMENTS

Figure 1:
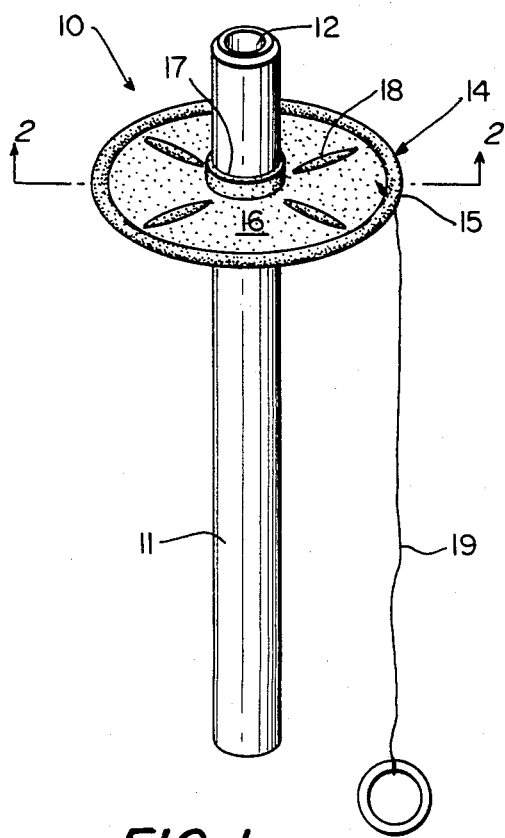
FIG. 1 is a side, perspective view of a rectal device in accordance with the present invention.

Referring now to the drawings, like elements are represented by like numerals throughout the several views.

Figure 4A:
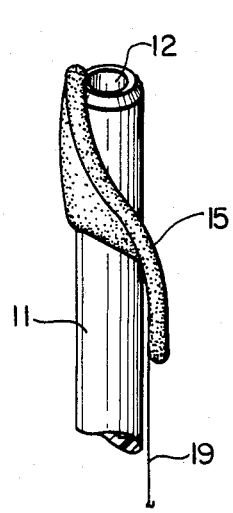
FIGS. 4A and 4B are partial perspective views similar to FIG. 1 but showing the rectal device being manipulated for insertion.
Figure 4B:
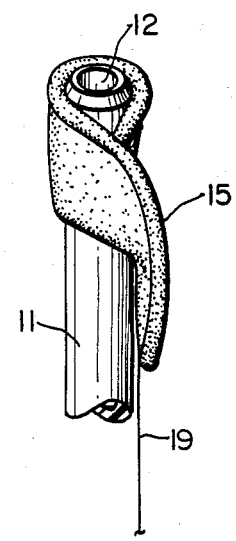

Referring to FIG. 1, there is shown a rectal device 10 comprising an elongated infusion tube 11 having an outlet 12 at the distal end thereof. An imperforate generally disc-shaped diaphragm 14 is attached at a collar 17 to the exterior of the tube 11. This diaphragm must be sufficiently stiff to normally assume a transverse position, generally perpendicular to the axis of the tube 12, as shown in FIGS. 1 and 2A, and yet sufficiently resilient to be folded up around the tube, as shown in FIGS. 4A and 4B.

Figure 2A:
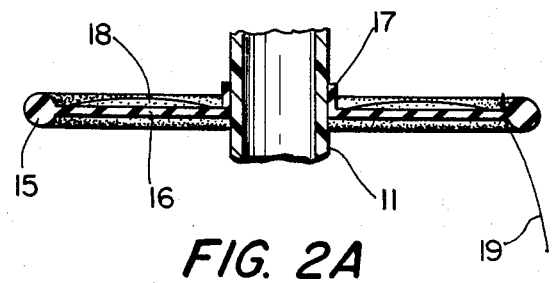
FIG. 2A is a partial cross-sectional view taken along line 2—2 of FIG. 1.
Figure 2B:
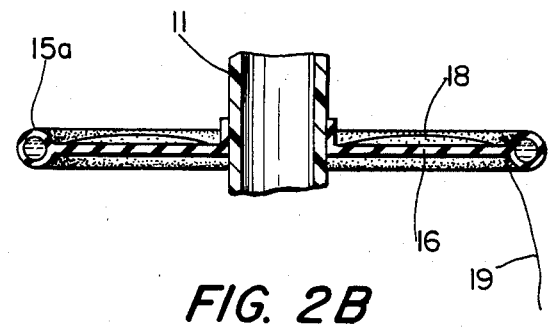
FIG. 2B is a partial cross-sectional view similar to FIG. 2A but showing a modification of the present invention.

For this purpose, the outer periphery of the diaphragm may be formed as an enlarged cross-section ring 15 of toroidal shape which may either be solid as shown in FIG. 2A or filled with a fluid, i.e. either a gas or a liquid, as shown at 15a in FIG. 2B. The central portion 16 between the ring 15 and the collar 17 is thinner and more pliable. To assist in striking the balance between the correct degree of stiffness and the correct degree of resilience, it has been found desirable to enhance the stiffness of the central portion 16. In the embodiment of FIG. 1, this is accomplished by moulding the diaphragm with upstanding ribs 18 which preferably extend radially, and in a perfered arrangement such ribs may be spaced equiangularly about the axis of the tube 11.

Figure 3:
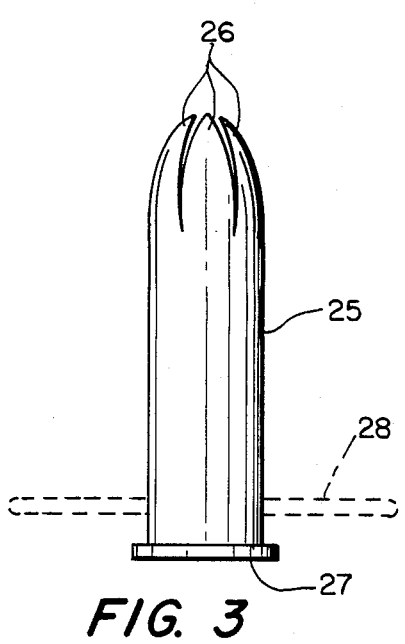
FIG. 3 is an enlarged side elevational view of an inserter tube to be used with the present invention.

FIG. 3 illustrates an inserter tube to be used in combination with the rectal infusion device of the present invention. Referring to FIG. 3, this inserter tube 25 includes a rounded but expandable distal end 26 formed with a plurality of finger like portions separated by slits, the material of the insert tube 25 being sufficiently resilient that these fingers 26 are capable of expanding outwardly to enlarge the distal end of the inserter tube. The tube 25 is completely open down to its enlarged proximal end 27. Shown in dotted lines in FIG. 3 is an insertion limiter 28 which may optionally be provided on the tube 25, which limiter would engage the outside of the anal opening to limit further movement of the inserter therethrough.

Referring now to FIGS. 3 through 6, a method of inserting the rectal device of FIGS. 1 and 2 will now be described.

First, the diaphragm is lubricated and folded or rolled up around the tube as shown in FIGS. 4A and 4B. In FIG. 4A the diaphragm has simply been folded such that the plane of the ring 15 comes as close as possible to the axis of the tube 11. Thereafter, as shown in FIG. 4B, the side portions of the ring spaced the farthest from the tube 11 are then folded around the tube. In this position the rectal device is inserted through the proximal end 27 of the inserter tube 25 and positioned therein as shown in FIG. 5. The tube 25, with the device 10 therein, is then introduced through the anal opening, as shown in FIG. 5, past the anal sphincter muscles 30 onto the rectal sling area 60. After the stage shown in FIG. 5, the operator may grasp the tube 11 and push the device 10 further up into the rectum and/or concurrently pull the inserter tube 25 down over the device 10. Soon the stage will be reached, as shown in FIG. 6, at which the diaphragm 14 is free of the inserter tube 25, whereby it is free to expand transversely, as shown in FIG. 6. Movement of the inserter tube 25 down along the tube 11 is then continued until tube 25 comes off of the tube 11, at which time it is discarded. An external stabilizer 32, formed of a suitably resilient material, can then be snapped into place on the tube 11 and slid up against the exterior of the anal opening to properly position the tube and diaphragm in place. If the device is to be used as an infusion device, the proximal end of tube 11 is then connected to a suitable fluid source and the liquid is introduced through the tube 11 and the outlet 12 into the rectum. If the device is to be used as an occluder, tube 11 is simply clamped.

After the medical procedure has been completed and it is desired to remove the device 10, the patient is taken to the appropriate location for removal, and a slow but firm pulling of the removal cord 19 will then cause sufficient movement of the diaphragm 14 to bring at least the edge to which the cord is attached toward the tube 11 enough to facilitate removal of the diaphragm 14 and hence the entire device 10 out through the anal opening.

FIG. 7 illustrates two modifications of the embodiment of FIG. 1, each of which modification can be utilitzed separately.

The first modification includes an alternate means for further stiffening the diaphragm 14. Instead of the ribs 18, or in combination with the ribs 18, there may be provided flexible band struts 34 connected at one end to the ring 15 and connected at the opposite end to a collar 36 which is in turn connected to the distal end of the tube 11.

Another modification includes the use of a second tube such as 35. In the event that it is desired to utilize the embodiment of FIG. 1 to introduce two fluids such as barium and air for a double contrast barium enema, one fluid may be introduced through the tube 35 While the other fluid would be introduced into the tube 11, into the area surrounding the tube 35.

Figure 8:
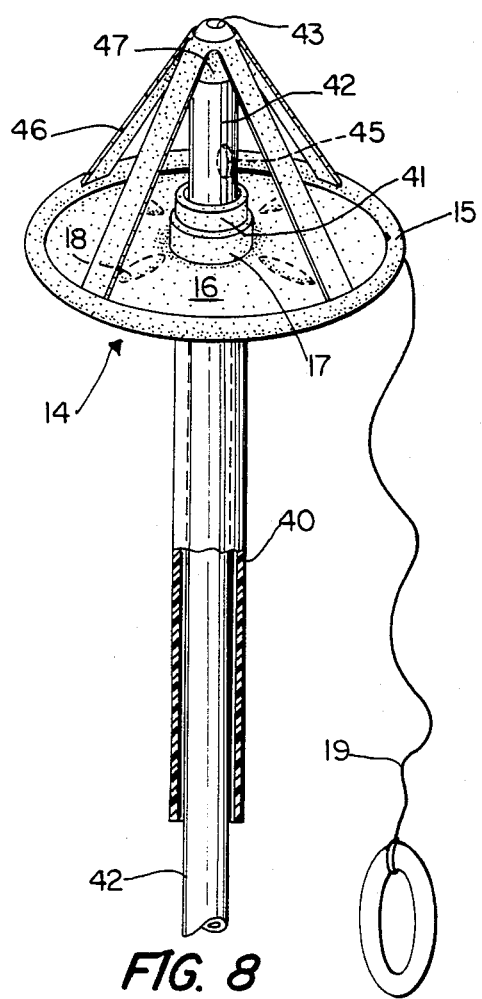
FIG. 8 is a side, perspective view similar to FIGS. 1 and 7 but showing another embodiment of the present invention.
Figure 9:
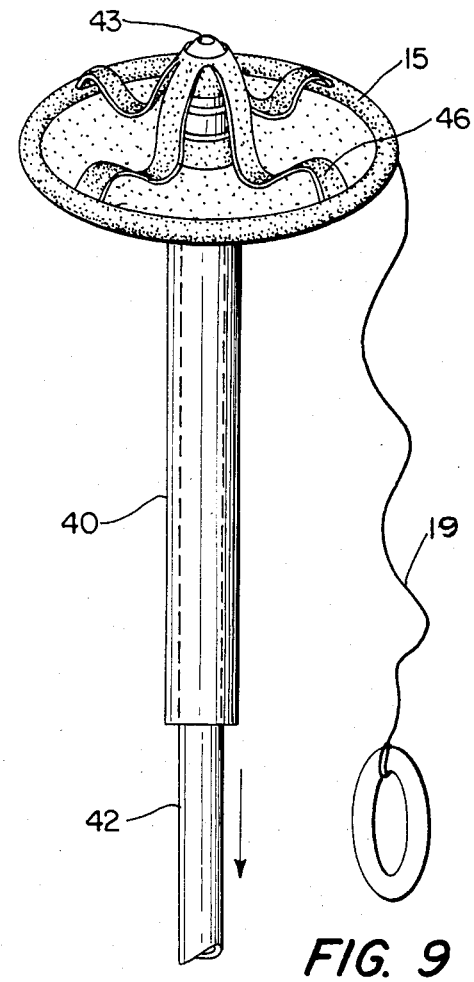
FIG. 9 is a side, perspective view similar to FIG. 8 but showing the parts in a different position.

FIGS. 8 and 9 illustrate another embodiment of the present invention. This embodiment differs from the embodiment of FIG. 1 in that it is provided with a pair of concentric tubes. The outer infusion tube 40 terminates at a distal outlet 41. The collar 17 is connected adjacent this distal outlet 41. An inside tube 42 extends completely through the tube 40, and is slideable axially relative thereto, and terminates at a distal outlet opening 43. Optionally, the distal end can be closed with the outlet openings provided as shown at 45 on the side of the tube 42.

In this embodiment the additional stiffening means may also comprise ribs 18, fins, as described below with respect to FIGS. 11 and 12, or flexible band struts 46. In this case the band struts would be connected at one end to the outer periphery of the diaphragm 14 and at their other ends to a collar 47 connected to the distal end of the inside tube 42. In the two tube embodiment a means should be provided for limiting axial movement of the tube 42 relative to the tube 40. It is therefore advantageous to use the band strut type stiffening means in this embodiment since these struts can serve the dual purpose of both providing additional stiffening means for the diaphragm and also limiting movement of the tube 42 axially within the tube 40.

FIG. 9 illustrates the embodiment of FIG. 8 with the tube 42 moved axially relative to the tube 40 such that the distal end 43 of the tube 42 is essentially adjacent the distal end 41 of the tube 40. This is the position which this device would assume during the introduction of the device into the anal opening. Also, in this embodiment, and if one ultilized the outlet openings 45 on the side of the tube 42, with a closed distal end of the tube 42, then these outlet openings would be concealed and not opened until subsequent axial extension of the tube 42 relative to the tube 40.

Figure 10A:
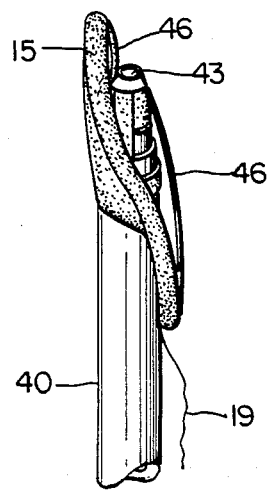
FIGS. 10A and 10B are partial side perspective views showing the embodiments of FIGS. 7 through 9 being manipulated to facilitate insertion thereof into the body.
Figure 10B:
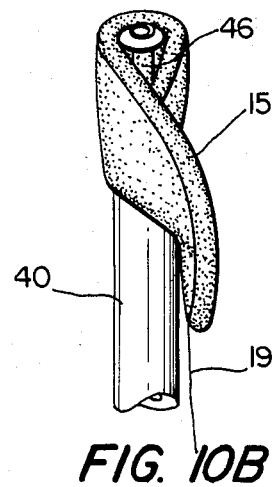

One method of introducing the embodiment of FIGS. 8 and 9 into the anal opening is essentially the same as the method described above with respect to the embodiment of FIG. 1. The one difference, as mentiond above, is that the device would intially assume the position as shown in FIG. 9. FIGS. 10A and 10B then illustrate the procedure for manipulating the diaphragm, which procedure is similar to that shown in FIGS. 4A and 4B, whereby the diaphragm is turned and then folded about the tube. Thereafter, it would be inserted into the inserter tube 25 and introduced as shown in FIGS. 5 and 6. With this embodiment, there would be one additional step. After removal of the inserter tube 25, the operator would grasp the proximal end of tube 42 and move this tube axially, distally to an extent limited by limiting means. For example, if the limiting means were the struts, the tube 42 would be moved until it assumed the position as shown in FIG. 8.

Thereafter, the stablizer element 32 would be applied and each of the tubes 40 and 42 would be connected to their appropriate fluid sources. And as with the embodiment of FIG. 1, after use a firm, slow pull on the cord 19 would facilitate removal of the diaphragm and also the tube out through the anal opening.

Figure 11:
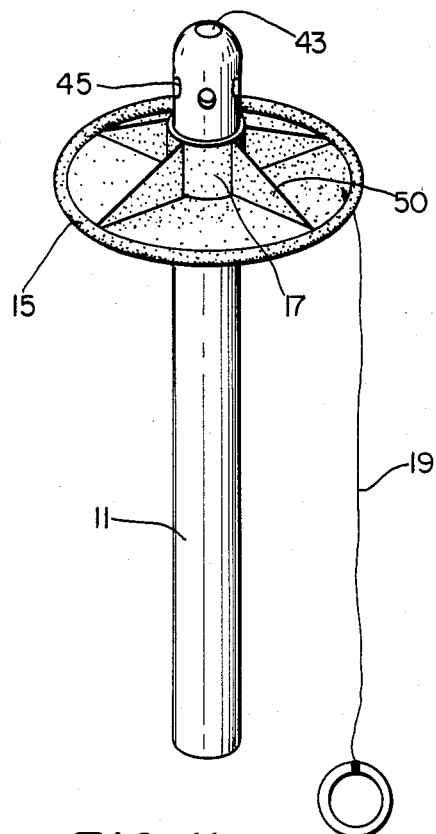
FIG. 11 is a perspective view similar to FIG. 1 but showing still another modification of the present invention.
Figure 12:
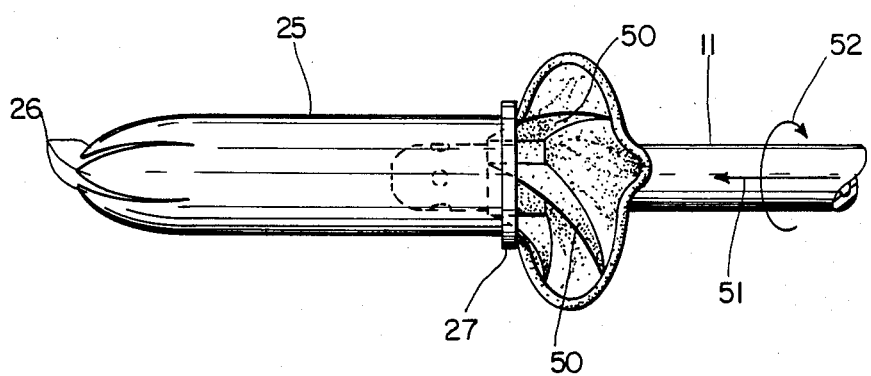
FIG. 12 is a side elevational view illustrating the insertion of the embodiment of FIG. 11 into an inserter tube.

The embodiment of FIG. 11 differs from the previously described embodiments in that the stiffening means comprises relatively high thin fins 50 which are preferably formed integrally with the central portion of the diaphragm, extending upwardly therefrom. These fins preferably increase in height from the outer periphery of the diaphragm, whereat they connect with the ring 15, to the interior of the diaphragm whereat they connect to the collar 17. It has been found that these upstanding ribs provide a particulary advantageous balance between sufficient flexibility to facilitate and sufficient ridgidity to remain in place during use.

Another advantage of the embodiment shown in FIG. 11 is that it lends itself to a somewhat more simplified method of insertion into the inserter tube. As shown in FIG. 12, the distal end of the device is placed up against the lower or proximal end of the inster tube 25. Then, with a forward twisting motion, as shown by the arrows 51 and 52 in FIG. 12, the device of FIG. 11 tends to wrap itself around the tube 11, permitting insertion thereof completely into the tube 25. This insertion method shown in FIG. 12, while particularly suitable for the embodiment of FIG. 11, can also be used to insert the embodiments shown in FIGS. 1, 7, 8 and 9, although this insertion method is far less efficient when utilized with respect to these earlier embodiments.

Although the invention has been described in considerable detail with respect to perfered embodiments thereof, it will be apparent that the invention is capable of numerous modifications and variations, apparent to those skilled in the art, without departing from the spirit and scope of the invention.

I claim:
1. A rectal device comprising:
    an elongated tube having a distal end and an outlet in the vicinity of the distal end, for introducing liquid into the anal opening through said outlet,
    a diaphragm attached to the side of the tube, near the distal end thereof, said diaphragm normally extending outwardly, transversely to the tube axis, such that in use, with the tube inserted in the person's rectum, the diaphragm rests against the inside of the anal opening, interiorly of the anal spincter muscles, to prevent the escape of fluid being introduced,
    said diaphragm having a relatively stiff outer ring and a more pliable imperforate central portion between the ring and the tube, the ring and central portion, taken together, being sufficiently stiff to maturally assume said transverse position, and sufficiently resilient to fold closely against the tube for insertion.
2. A rectal device according to claim 1, including further stiffening means, in addition to the ring, for assisting the diaphragm to normally assume said transverse position.
3. A rectal device according to claim 2, said further stiffening means including upstanding ribs formed into the central portion.
4. A rectal device according to claim 3, said ribs extending radially and being upstanding portions of the material of the central portion.
5. A rectal device according to claim 2, said further stiffening means comprising a plurality of flexible band struts extending from the ring to the tube, connected to the tube on the distal side of the diaphragm.
6. A rectal device according to claim 2, said stiffening means comprising thickened ribs extending radially within the central portion and formed of the material of the central portion.
7. A rectal device according to claim 1, in combination with an inserter tube having a rounded expandable distal end, the internal diameter of the inserter tube being of a size to and receiving the elongated tube, with the diaphragm wrapped therearound, whereby the rectal device is inserted in the anal opening while inside the inserter tube, after which the distal end of the inserter tube expands as the inserter tube is slid down over the elongated tube, leaving the infusion tube in the anal opening with the diaphragm assuming its transverse position.
8. A rectal device according to claim 7, including exterior limiting means on the outside of the inserter tube to limit the amount of its movement into the anal opening.
9. A rectal device according to claim 1, comprising an inside elongated tube having a distal end, said inside tube being located within the outer, first said enlongated tube, and spaced therefrom enough to permit the flow of fluid between the tubes, said inside tube having an outlet opening in the vicinity of its distal end, whereby two different fluids can be introduced, one fluid within the inside tube and another fluid between the two tubes.
10. A rectal device according to claim 9, including limiting means for limiting the axial movement of the inside tube, relative to the outer tube.
11. A rectal device according to claim 10, said limiting means comprising a plurality of flexible band struts extending from the ring to the distal end of the inside tube, said struts also serving to assist the stiffening of the diaphragm to normally assume its transverse position when the inside tube is elongated distally relative to the outer tube.
12. A rectal device according to claim 9, the inside tube outlet being located on the side thereof, near its distal end, such that said outlet opening is covered by the outer tube when the inside tube is withdrawn into the outer tube.
13. A rectal device according to claim 1, including a cord attached to the ring to facilitate removal of the rectal device after use.
14. A rectal device according to claim 1, including a stabilizer means for attachment to the elongated tube, exterior of the person's body, after insertion of the rectal device, to prevent unintended farther movement of the rectal device into the anal opening.
15. A rectal device comprising an elongated tube, having a distal end a diapharagm attached to the side of tube, near the distal end thereof, said diaphragm normally extending outwardly, transversely to the tube axis, such that in use, with the tube inserted in the person's rectum, the diaphragm rests against the inside of the anal opening, interiorly of the anal sphincter muscles, to prevent the escape through the anal opening of substances within the rectum,
    said diaphragm having a relatively stiff outer ring and a more pliable imperforate central portion between the ring and tube, the ring and central portion, taken together, being sufficiently stiff to naturally assume said transverse position, and sufficiently resilient to fold closely against the tube for insertion.
16. A method of inserting a rectal device into the anal opening, comprising:
    taking an elongated tube having a diaphragm attached to the side thereof, which diaphragm is sufficiently stiff to normally assume a transverse position relative to the tube, and sufficiently resilient to wrap around the tube,
    wrapping the diaphragm around the tube, inserting the tube with the wrapped diaphragm into an inserter tube, asid inserter tube having a rounded, expandable distal end and a proximal end, inserting the inserter tube, with the elongated tube located therein, into the anal opening until the diaphragm has passed the anal sphincter muscles, and then removing the inserter tube by moving it down along the elongated tube, which remains stationary, whereby the said expandable distal end of the inserter tube expands to pass over the elongated tube and diaphragm, leaving the diaphragm free to expand within the rectum to block the anal opening to prevent the escape of substances located within the rectum.

17. A method according to claim 16, wherein the elongated tube comprises inner and outer tubes, the diaphragm being connected to the outer tube, and the inner tube being slideable within the outer tube, and including the step of moving the inner tube distally relative to the outer tube, after the inserter tube has been removed, to an extent limited by struts interconnecting the outer periphery of the diaphragm with a distal end of the inner tube.

18. A method according to claim 16, wherein the wrapping step includes folding the diaphragm up against the elongated tube along one diameter thereof, and then folding the remainder of the diaphragm around the elongated tube.

19. A method according to claim 16, wherein the wrapping step is performed while pushing the distal end of the elongated tube into the proximal end of the inserter tube and twisting the inserter tube and diaphragm to cause wrapping of the diaphragm around the elongated tube.

20. A rectal device comprising:

an elongated tube having a distal end and an outlet in the vicinity of the distal end, for introducing liquid into the anal opening through said outlet, an imperforate generally disc shaped diaphragm attached to the side of the tube, near the distal end thereof, said diaphragm normally extending outwardly, transverse to the tube axis, such that in use, with the tube inserted in the person's rectum, the diaphragm rests against the rectal sling area inside of the anal opening, interior of the anal sphincter muscles, to prevent the escape of fluid being introduced, said generally disc shaped diaphragm being sufficiently stiff to naturally assume said transverse position and sufficiently resilient to seat itself within the rectal sling area above the anal sphincter muscles and to fold closely against the tube for insertion and removal.

21. A rectal device according to claim 20, including ribs formed into the diaphragm for increasing its stiffness for assisting the diaphragm to normally assume its said transverse position.

22. A rectal device according to claim 21, said ribs extending radially and formed of the material of the diaphragm.

23. A rectal device according to claim 20, including a plurality of flexible band struts extending from the outer periphery of the diaphragm to the elongated tube and connected to the tube on the distal side of the diaphragm.

24. A rectal device according to claim 20, at least a portion of the diaphragm including a cavity filled with a fluid.

25. A rectal device according to claim 20, the diaphragm being located in the vicinity of said distal end of the tube.

26. A method of introducing liquid into an anal opening, comprising:

taking an elongated tube having a generally disc shaped imperforate diaphragm attached to the side thereof, which diaphragm is sufficiently stiff to normally assume a transverse position relative to the tube and sufficiently resilient to wrap around the tube, inserting the tube through the anal opening with the diaphragm wrapped around the tube until the diaphragm reaches the rectal sling area at which it moves resiliently out from the tube to assume its said normally transverse shape, and arranging the diaphragm within the rectum such that it seats on the rectal sling area to create a fluid seal, preventing leakage of fluid outwardly from the inside of the rectum, by engagement of the diaphragm with the rectal sling area.

* * * * *